United States Patent [19]
Weers et al.

[11] Patent Number: 5,840,177
[45] Date of Patent: Nov. 24, 1998

[54] QUATERNARY AMMONIUM HYDROXIDES AS MERCAPTAN SCAVENGERS

[75] Inventors: Jerry J. Weers, Ballwin; David R. Gentry, St. Louis, both of Mo.

[73] Assignee: Baker Hughes Incorporated, Houston, Tex.

[21] Appl. No.: 931,675

[22] Filed: Sep. 16, 1997

Related U.S. Application Data

[63] Continuation of Ser. No. 206,137, Mar. 3, 1994, abandoned.

[51] Int. Cl.$^6$ ..................................................... C10G 19/02
[52] U.S. Cl. ..................... 208/208 R; 208/207; 208/203; 208/206; 208/189
[58] Field of Search .................................... 208/208, 189, 208/207, 203

[56] References Cited

U.S. PATENT DOCUMENTS

| | | | |
|---|---|---|---|
| 3,468,640 | 9/1969 | Barusch | 44/75 |
| 4,594,147 | 6/1986 | Roof et al. | 208/207 |
| 4,867,865 | 9/1989 | Roof | 208/236 |
| 4,908,122 | 3/1990 | Frame et al. | 208/207 |
| 4,913,802 | 4/1990 | Bricker et al. | 208/207 |
| 4,929,340 | 5/1990 | Pollastrini et al. | 208/189 |
| 5,183,560 | 2/1993 | Roof et al. | 208/236 |
| 5,200,062 | 4/1993 | Poirier et al. | 208/236 |
| 5,273,646 | 12/1993 | Frame et al. | 208/189 |

FOREIGN PATENT DOCUMENTS

| | | | |
|---|---|---|---|
| 2064518 | 3/1992 | Canada | C10G 29/20 |
| 0 107 088 A1 | 5/1984 | European Pat. Off. | C07C 93/04 |
| 0 075 065 A3 | 9/1984 | European Pat. Off. | C07C 89/02 |
| 0 161 082 A3 | 8/1986 | European Pat. Off. | C10L 1/22 |
| 0 538 819 A3 | 4/1993 | European Pat. Off. | C10G 29/20 |
| 0538819 | 4/1993 | European Pat. Off. . | |

*Primary Examiner*—Helane Myers
*Attorney, Agent, or Firm*—Howell & Haferkamp, L.C.

[57] ABSTRACT

A method for scavenging mercaptans in a hydrocarbon fluid is disclosed. According to the method, an effective mercaptan-scavenging amount of an aqueous scavenging composition is added to the fluid. The composition comprises a quaternary ammonium hydroxide of the formula $R^1R^2R^3R^4NOH$. $R^1$ and $R^2$ are, independently, alkyl groups of from one to about eighteen carbon atoms, aryl groups of from six to about eighteen carbon atoms or alkylaryl groups of from seven to about eighteen carbon atoms. $R^3$ is an alkyl group of from two to about eighteen carbon atoms, an aryl group of from two to about eighteen carbon atoms or an alkylaryl group of from four to about eighteen carbon atoms. $R^2$ and $R^3$ may be joined to form a heterocyclic ring including the N and optionally an oxygen atom. $R^4$ is $-(CH_2CH_2O)_nH$, wherein n is an integer from one to about eighteen, or $-CHR^5CHR^6Y$, wherein $R^5$ and $R^6$ are, independently, hydrogen, alkyl groups of from one to about eighteen carbon atoms, aryl groups of from six to about eighteen carbon atoms or alkylaryl groups of from seven to about eighteen carbon atoms. Y is a non-acidic group. Related compositions and methods are also disclosed.

28 Claims, No Drawings

QUATERNARY AMMONIUM HYDROXIDES AS MERCAPTAN SCAVENGERS

This application is a continuation of Ser. No. 08/206,137 filed on Mar. 3, 1994, now abandoned.

BACKGROUND OF THE INVENTION

1. Field of the Invention

The present invention relates to the scavenging of mercaptans in hydrocarbon fluids and more particularly to the use of quaternary ammonium hydroxides as mercaptan scavengers.

2. Description of Prior Art

Hydrocarbon fluids, such as crude oil, crude oil emulsions, oilfield condensate, petroleum residua and even refined fuels often contain a variety of mercaptans, including mercaptans of relatively low molecular weight. Because of the volatility of mercaptans of relatively low molecular weight (for example, methyl mercaptan, $CH_3SH$, ethyl mercaptan, $CH_3CH_2SH$ and propyl mercaptan, $CH_3CH_2CH_2SH$), they tend to evolve into vapor spaces, where their offensive odors create problems in and around storage areas and throughout pipelines and shipping systems used for transporting the hydrocarbon.

Various additives have been employed in efforts to alleviate these problems. For example, choline or choline hydroxide has been found to alleviate hydrogen sulfide evolution and to scavenge mercaptans. See, for example, U.S. Pat. No. 4,594,147 to Roof et al., U.S. Pat. No. 4,867,865 to Roof and U.S. Pat. No. 5,183,560 to Roof et al. However, choline and choline hydroxide are not well suited for many uses and media, such as in crude oil. Although choline and choline hydroxide might scavenge mercaptans in such media, they also form a volatile and malodorous by-product with the sulfur compounds indigenous to such media. Accordingly, the use of choline and choline hydroxide to control odors associated with light weight mercaptans is self-defeating in media such as crude oil. Thus, the cited patents to Roof and Roof et al. fail to address this problem and instead describe the use of choline or choline hydroxide in the more refined fuel oils.

European application 0 538 819 A3 to Roof et al. describes the use of oil-soluble quaternary ammonium compounds of the formula

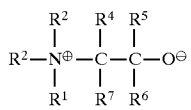

to scavenge various sulfur compounds, including mercaptans, from certain oils, especially high boiling, heavy residual fuels. These compounds, prepared under anhydrous conditions, are what are described herein as "internal ions"; i.e., the positive charge on the nitrogen and the negative charge on the oxygen result in overall electrically neutral compounds without the presence of counter ions such as halides. The European application stresses the significance of the oil solubility of these compounds, noting that they are more oil soluble than choline base and so disperse through the oil being treated more thoroughly to decrease the concentration of undesirable sulfur compounds more effectively. Nevertheless, the compositions of the European application suffer from certain disadvantages. For example, compositions that are produced in higher yields, yet still at low cost, and that reduce mercaptan concentrations more effectively are still desired.

Accordingly, despite the reports of these techniques, industry is still searching for other compositions and methods for scavenging low molecular weight mercaptans more effectively and more efficiently.

SUMMARY OF THE INVENTION

The present invention, therefore, is directed to a novel method for scavenging mercaptans in a hydrocarbon fluid. According to the method, an effective mercaptan-scavenging amount of an aqueous scavenging composition comprising a quaternary ammonium hydroxide is added to the fluid. The quaternary ammonium hydroxide may be represented by the formula $R^1R^2R^3R^4N+OH^-$. $R^1$ and $R^2$ are, independently, alkyl groups of from one to about eighteen carbon atoms, aryl groups of from six to about eighteen carbon atoms or alkylaryl groups of from seven to about eighteen carbon atoms. $R^3$ is an alkyl group of from two to about eighteen carbon atoms, an aryl group of from two to about eighteen carbon atoms or an alkylaryl groups of from seven to about eighteen carbon atoms. $R^2$ and $R^3$ may be joined to form a heterocyclic ring including the N and optionally an oxygen atom. $R^4$ corresponds to the formula $—(CH_2CH_2O)_nH$, wherein n is an integer from one to about three or more, or the formula $—CHR^5CHR^6Y$, wherein $R^5$ and $R^6$ are, independently, hydrogen, alkyl groups of from one to about eighteen carbon atoms, aryl groups of from six to about eighteen carbon atoms or alkylaryl groups of from seven to about eighteen carbon atoms, and Y is a non-acidic group corresponding to the formula $—OH$, $—SR^7$ or $—NR^7R^8$, wherein $R^7$ and $R^8$ are, independently, hydrogen, alkyl groups of from one to about eighteen carbon atoms, aryl groups of from six to about eighteen carbon atoms or alkylaryl groups of from seven to about eighteen carbon atoms.

The present invention also is directed to a novel method for preparation of a quaternary ammonium hydroxide. According to the method, a tertiary amine is reacted with ethylene oxide or propylene oxide in the presence of water. The tertiary amine corresponds to the formula $R^1R^2R^3N$, wherein $R^1$, $R^2$ and $R^3$ are defined as in the preceding paragraph and $R^2$ and $R^3$ may be joined to form a heterocyclic ring including the N and optionally an oxygen atom. The method produces a quaternary ammonium hydroxide of the formula $R^1R^2R^3R^4N^+OH^-$, wherein $R^1$, $R^2$ and $R^3$ are as defined above and $R^4$ is

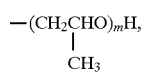

wherein m is 1, 2 or 3.

Among the several advantages of this invention, may be noted the provision of a method for scavenging mercaptans more effectively and efficiently than in conventional methods; the provision of such method that scavenges selectively for light weight mercaptans versus heavier weight mercaptans; the provision of such method that does not tend to generate new malodorous compositions; and the provision of a method for making a scavenging composition useful in such method.

DETAILED DESCRIPTION OF THE PREFERRED EMBODIMENTS

In accordance with the present invention, it has been discovered that certain quaternary ammonium hydroxides are surprisingly effective mercaptan scavengers that scavenge low weight mercaptans selectively in preference to higher weight mercaptans. The efficacy of the hydroxides is especially surprising in view of the findings that the hydroxides are significantly more effective scavengers than compounds differing only in the counter ion (i.e., it is other than hydroxide), and that in preferred cases the hydroxides are even more effective mercaptan scavengers than the corresponding internal ions (i.e., $R_3N+R'O^-$ where $R_3N^+R'OH$ $OH^-$ is the preferred hydroxide).

The selectivity of the hydroxides reduces the waste that would otherwise be encountered in scavenging higher weight mercaptans unnecessarily, and so permits scavenging of the less desirable mercaptans with relatively small amounts of the hydroxides. And, even though the noted European application stresses the importance of the oil-solubility of its compounds to their efficacy, the superior efficacy of the hydroxides in scavenging mercaptans in hydrocarbons has been found even though the hydroxides would be expected to be significantly less oil-soluble than their corresponding internal ions.

Moreover, it has been found that introducing oxygen such as by sparging the treated fluid with air increases the scavenging activity dramatically.

The quaternary ammonium hydroxide may be represented by the formula $R^1R^2R^3R^4N^+OH^-$. $R^1$ and $R^2$ are, independently, alkyl groups of from one to about eighteen carbon atoms, aryl groups of from six to about eighteen carbon atoms or alkylaryl groups of from seven to about eighteen carbon atoms. $R^3$ is an alkyl group of from two to about eighteen carbon atoms, an aryl group of from two to about eighteen carbon atoms or an alkylaryl groups of from seven to about eighteen carbon atoms. $R^4$ corresponds to the formula $-(CH_2CH_2O)_nH$, wherein n is an integer from one to about three or more, the formula

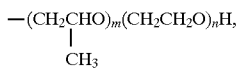

wherein m and n are integers from zero to about eighteen (independently selected except that m+n is at most about eighteen), or the formula $-CHR^5CHR^6Y$, wherein $R^5$ and $R^6$ are, independently, hydrogen, alkyl groups of from one to about eighteen carbon atoms, aryl groups of from six to about eighteen carbon atoms or alkylaryl groups of from seven to about eighteen carbon atoms, and Y is a non-acidic group corresponding to the formula $-OH$, $-SR^7$ or $-NR^7R^8$, wherein $R^7$ and $R^8$ are, independently, hydrogen, alkyl groups of from one to about eighteen carbon atoms, aryl groups of from six to about eighteen carbon atoms or alkylaryl groups of from seven to about eighteen carbon atoms. Preferably, $R^4$ is $-(CH_2CH_2O)_nH$ or $-CHR^5CHR^6Y$, wherein n, $R^5$, $R^6$ and Y are defined as above.

In choline base, each of $R^1$, $R^2$ and $R^3$ is methyl. It now has been found that if one of $R^1$, $R^2$, and $R^3$ is longer than methyl, scavenging may be carried out even in crude oil without the volatile, malodorous scavenging by-products trimethylamine generated with use of the choline base. Accordingly, $R^3$ has been designated as the radical having at least two carbon atoms. In preferred forms, $R^1$ and $R^2$ are alkyl groups of eighteen or fewer carbon atoms and, more preferably, lower alkyl groups of six carbons or fewer, especially three carbons or fewer and, optimally, methyl groups. Most desirably, $R^3$ is a fatty group, such as from about eight to about eighteen carbon atoms, especially about ten to about fourteen carbons atoms, such as a coco- group. However, alternatively, $R^3$ may be a benzyl group or substituted aryl groups, for example, alkylbenzyl groups such as methyl benzyl, or, less desirably, even may be an alkyl group of at least about two carbon atoms. In other, less preferred, embodiments, $R^2$ and $R^3$ may be joined to form a heterocyclic ring including the N and optionally an oxygen atom. In the latter case, a morpholine may be formed. Such ring products have been found to be less effective than the other products and more difficult to prepare by oxyalkylation of a tertiary amine.

$R^4$, as noted, corresponds to the formula $-(CH_2CH_2O)_nH$, wherein n is an integer from one to about eighteen, the formula

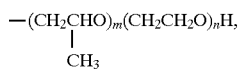

wherein m and n are integers from zero to about eighteen (independently selected except that m+n is at most about eighteen), or the formula $-CHR^5CHR^6Y$, wherein $R^5$ and $R^6$ and Y are defined as above. Inclusion of such $R^4$ groups in the quaternary compound have been found to increase the performance of the compound as a mercaptan scavenger significantly over that of tetra-alkyl quaternary compounds. In the preferred embodiment, $R^4$ corresponds to the formula $-CHR^5CHR^6Y$, wherein $R^5$ and $R^6$ are hydrogen or lower alkyls of fewer than about six carbon atoms, especially hydrogen, and Y is $-OH$.

However, when the quaternary compound is prepared by reacting a tertiary amine with an alkylene oxide to form a quaternary compound wherein $R^4$ is $-CH_2CH_2OH$, quaternary compounds are also formed wherein $R_4$ is the ether or polyether group $-(CH_2CH_2O)_nH$. Thus, a composition containing quaternary compounds wherein $R^4$ is $-CH_2CH_2OH$ often also contains quaternary compounds wherein $R_4$ is the ether or polyether group $-(CH_2CH_2O)_nH$. Generally, however, if the quaternary compound is prepared by oxyalkylating a tertiary amine, the amine is reacted with the alkylene oxide in a molar ratio of about 1:1 so that, while some amine remains unreacted thereby leaving some alkylene oxide available for polyether formation, typically the ether or polyether chains that do form are short; n being mostly one, two or three.

The quaternary ammonium hydroxides of this invention may be prepared by a variety of known techniques that will be readily apparent to those of ordinary skill in the art. For example, the quaternary ammonium hydroxides may be prepared by ion exchange techniques from readily available quaternary ammonium halides, such as quaternary ammonium chlorides. By such techniques, the quaternary ammonium halides may be passed through an ion exchange column for exposure to an ion exchange resin, exchanging the halide ion for $OH^-$ ions (or $Y^-$ ions where Y is as defined above and does not correspond to OH) from the column. Thus, according to this method for producing the hydroxide, the halide $R^1R^2R^3R^4N^+Z^-$, wherein $R^1$, $R^2$, $R^3$ and $R^4$ are as defined in the broader definition above and $Z^-$ is a halide, is brought into contact with an ion exchange resin bearing hydroxide ions to form $R^1R^2R^3R^4N^+OH^-$.

Alternatively, the quaternary ammonium hydroxides of this invention may be prepared by oxyalkylation of tertiary amines in the presence of water. Techniques for oxyalkylation of tertiary amines have been described, for example, in the European patent application noted above, but the European application requires the reaction to be carried out under anhydrous conditions. Anhydrous conditions were necessary for the formation of the internal ions of the European application. Now, however, the benefits of the hydroxides have been discovered. Such compounds are formed when the oxyalkylation is carried out in the presence of water. And, surprisingly, it has been discovered that the reaction carried out in the presence of water results in yields of the quaternary ammonium hydroxide product that are significantly higher than the yields of quaternary ammonium internal ion resulting from the reaction carried out under anhydrous conditions. Moreover, carrying out the reaction in the presence of water allows the use of less oxide per amine than called for in the nonaqueous reaction of the European application of Roof et al. (that is, a 1:1 molar ratio may be employed as opposed to bubbling the oxide through the amine as called for by Roof et al.). In addition, the non-aqueous reaction proceeds much faster than does the non-aqueous reaction and so the quaternary product may be formed in much less time. Where Y of $R^4$ is a non-acidic group other than $OH^-$, a similar reaction may be carried out with, for example, an alkylene sulfide or alkyleneimine instead of an alkylene oxide.

Thus, the subject inventor has discovered that if the oxyalkylation reaction is carried out in the presence of water, the resulting quaternary ammonium hydroxides not only are more effective mercaptan scavengers in certain preferred cases than are the internal ions that would have been produced had the reaction taken place in the absence of water, but also are produced in higher yields than the internal ions would have been.

Accordingly, in more detail, where $R^4$ of the quaternary ammonium hydroxide $R^1R^2R^3R^4N+OH^-$ is hydroxyethyl or hydroxypropyl, or if $R^4$ is an ether or polyether group as described above, the hydroxide may be prepared by reacting a tertiary amine such as of the form $R^1R^2R^3N$ with an alkylene oxide, in the presence of water. The alkylene oxide may be propylene oxide, but ethylene oxide is preferred. In the less preferred cases where the quaternary ammonium compound $R^1R^2R^3R^4N^+$ is not a hydroxide, but $R^4$ corresponds to the formula $—CHR^5CHR^6Y$, wherein $R^5$ and $R^6$ are defined above and Y is a non-acidic group corresponding to the formula $—SR^7$ or $—NR^7R^8$, an alkylene sulfide or alkyleneimine, respectively, may be substituted for the alkylene oxide and otherwise the same procedures may be followed.

$R^1$, $R^2$ and $R^3$ of the tertiary amine are as defined above. Preferably, however, $R^1$ is methyl and more preferably $R^2$ is also methyl. Although $R^2$ and $R^3$ may be joined to form a heterocyclic ring including the N and optionally an oxygen atom, such as to form a morpholine derivative, such compositions have been found to be more difficult to oxyalkylate without the offset of producing more potent scavengers and so in the most desirable configurations, $R^2$ and $R^3$ are not joined. Preferably, $R^3$ is a fatty group of from about six to about twelve carbon atoms.

The reaction is carried out in an aqueous solvent. For example, the solvent may comprise about 50% by weight to about 95%, by weight alcohol such as isopropanol or, preferably, methanol, and about 5% by weight to about 50% by weight water. A typical solvent formulation, therefore, might comprise, by weight, two parts solvent to one part water.

The active ingredients may make up about 70% by weight of the reaction mixture (the remaining 30% being solvent). In a preferred method of preparation, the tertiary amine is stirred in the solvent and the system is pressurized with alkylene oxide added in a molar ratio of about 1:1 to the amine. Generally, the molar ratio is in the range of from about 1:1 to about 1.5:1 alkylene oxide to amine. The reaction is carried out at a temperature typically under about 70° C., preferably about 40° C. to about 50° C., with continuous stirring and its completion is signalled by a drop in pressure to about atmospheric. The resulting mixture, aside from unreacted solvent, is a combination of the quaternary compounds wherein the $R^4$'s are of the formulae $—CH_2CH_2OH$ and $—(CH_2CH_2O)_nH$, wherein n is as defined above, unreacted amine, and glycols formed from reaction of the alkylene oxide and water. Other quaternary ammonium hydroxides wherein $R^4$ corresponds to the formula

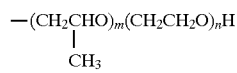

or the formula $—CHR^5CHR^6Y$ wherein m, n, $R^5$, $R^6$ and Y are as defined above, may be prepared by similar techniques that will be readily apparent to those of ordinary skill in the art.

The resulting quaternary ammonium hydroxide may be added to the medium to be treated by standard techniques, such as by injection or simple pouring and it may be dispersed throughout the fluid by stirring or other agitation. The additive is incorporated at a level sufficient to scavenge the mercaptans to a desired degree and will depend on the mercaptan content of the medium and the corresponding stoichiometry. However, typical additive levels may be on the order of about 100 to about 10,000, preferably about 500 to about 5,000, ppm based on the weight of the medium to be treated.

The medium may be any hydrocarbon fluid, preferably a liquid. For example, excellent results have been obtained from treatment of crude oil, petroleum residua and fuels such as kerosene. It should be recognized that while the fluids are referred to as hydrocarbon fluids, in some cases (for example, crude oil emulsions), hydrocarbons may make up less than half of the fluid by weight. The product is particularly useful for treatment of crude oil in that it does not add an additional malodorous compound as has been associated with the use of choline to treat crude oil. However, results superior to those achieved with the use of other compositions such as the internal ion of the noted European application have been found with respect to a variety of hydrocarbon media.

In addition, even significantly greater degrees of scavenging have been found to result if the medium is first oxygenated such as by aeration prior to addition of the mercaptan scavenger. Although the subject inventor does not wish to be bound by any particular theory, it is believed that the mechanism by which this scavenging occurs is according to the following reaction sequence wherein $R^1R^2R^3R^4N^+$ $OH^-$ is the scavenger and RSH is the mercaptan:

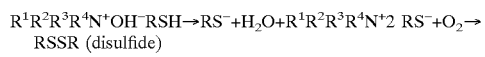

Thus, increasingly improved results have been noted as the amount of oxygen added such as by aerating or bubbling air into the medium increases to 100% of the stoichiometry of this reaction scheme. Addition of air in an amount beyond 100% has not been found to improve scavenging much more than that associated with addition of 100% of stoichiometry.

Effective scavenging may be carried out at the ambient temperature of the hydrocarbon fluid (e.g., about 20° C. for stored crude oil, residuum or fuel), but the performance of the scavenger has been found to be improved at higher temperatures such as about 50° C. to about 75° C. The scavenger tends to decompose at even higher temperatures, such as at about 100° C. However, the decomposition at such temperatures occurs relatively slowly while the time for the reaction between the scavenger and the mercaptans is relatively short, generally requiring only several hours to reduce the mercaptan level substantially. Thus, the scavenger may still be employed at such elevated temperatures with good results.

The quaternary ammonium scavengers of this invention have been found to react selectively with the lower molecular weight mercaptans without imparting to the system an odor of its own. More particularly, for example, the scavengers have been found to scavenge methyl mercaptan in preference to ethyl mercaptan and to scavenge ethyl mercaptan in preference to n-propyl mercaptan and to scavenge n-propyl mercaptan in preference to n-butyl mercaptan, and so forth. It also has been observed that the scavengers react selectively with linear mercaptans over branched mercaptans. Thus, the scavengers enable removal of the most volatile mercaptans, which are the greatest contributors to odor problems, with limited waste of scavenger on side reactions with less volatile mercaptans.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples, all percentages are given on a weight basis unless otherwise indicated.

EXAMPLE 1

A tertiary amine (ADMA WC Amine, Ethyl Corp., 77 g, 0.35 mole), methanol (92.4 g) and water (12.6 g, 0.70 mole) were placed in a glass autoclave fitted with cooling coils, stirrer, thermowell and ethylene oxide delivery tube. The reactor was sealed and ethylene oxide (15.4 g, 0.35 mole) was added in one portion, with nitrogen used to aid the addition. Immediately after the addition of ethylene oxide, the reactor had a total pressure of 20 pounds per square inch and a pot temperature of 20° C. After one hour, a maximum temperature of 26° C. had been reached. The pressure fell off to 16 psi after 90 minutes.

The product was analyzed by titration and contained 1.22 meq/g of quaternary ammonium hydroxide and 0.57 meq/g of tertiary amine. The relative yields are shown in Example 8.

EXAMPLE 2

The same procedure as followed in Example 1, except that water was omitted, was used to prepare an internal salt compound as disclosed in the noted European application to Roof et al. Thus, 80.1 g (0.364 mole) of the amine in 96.1 g methanol were reacted with 16.0 g (0.364 mole) ethylene oxide. After 90 minutes, the product contained 1.23 meq/g quaternary ammonium hydroxide and 0.72 meq/g tertiary amine. The relative yields are shown in Example 8.

EXAMPLE 3

Various quaternary ammonium hydroxides were prepared from alkoxylated tertiary amines and added to samples of 50° C. crude oil containing 169.82 ppm 1-propane thiol (propyl mercaptan) and the resulting 1-propane thiol concentrations were measured. The results are reported in the following table, wherein each quaternary ammonium hydroxide is identified by the tertiary amine and the alkylene oxide ("ALKOXIDE", either ethylene oxide, referred to as EtO, or propylene oxide, referred to as PrO), the concentrations of the quaternary ammonium hydroxide ("QUAT CONTENT") and the unreacted amine ("UNREACTED AMINE CONTENT") in the samples are given in milliequivalents per gram, and the 1-propane thiol concentration in the sample after treatment as measured according to ASTM D-3227 is given in ppm. In the table, "% REDUCTION" refers to the percentage of reduction of 1-propane thiol that was achieved.

| TERTIARY AMINE | ALKOX-IDE | QUAT CONTENT | UNREACTED AMINE CONTENT | 1-PROPANE THIOL CONTENT | % REDUCTION |
|---|---|---|---|---|---|
| Blank | | | | 169.82 | |
| Methyl-morpholine | EtO | 2.04 | 0.96 | 127.71 | 25 |
| Dimethylcoco | EtO | 1.23 | 0.61 | 119.86 | 29 |
| 2-hydroxyethylmorpholine | EtO | 0.54 | 2.34 | 126.49 | 26 |
| Dimethyl-benzyl | EtO | 0.812 | 1.624 | 88.26 | 48 |
| Dimethylcoco | PrO | 0.847 | 1.493 | 160.74 | 5 |
| Methyl-morpholine | EtO | 1.334 | 1.66 | 75.38 | 56 |
| Dimethyl-ethanol | EtO | 3.85 | 0.40 | 112.55 | 34 |
| Dimethylcoco | EtO | 1.26 | 1.17 | 110.19 | 35 |

EXAMPLE 4

Mercaptan selectivity of 70% N-(2-hydroxyethyl)-N,N-dimethyl-N-coco ammonium hydroxide in an isopropanol and water solution was measured in 50° C. crude oil by GC analysis (using a sulfur specific detector) about two hours after addition of 1000 ppm of the hydroxide. A second sample of the scavenger was prepared and tested in the same manner. The following table shows the mercaptan content (in ppm) of the crude oil for each of various mercaptans (identified by type of thiol) before and after treatment and the corresponding percentage reduction of that mercaptan.

| | | FIRST SCAVENGER | | SECOND SCAVENGER | |
|---|---|---|---|---|---|
| MERCAPTAN | INITIAL CONTENT | CONTENT AFTER TREATMENT | % REDUCTION | CONTENT AFTER TREATMENT | % REDUCTION |
| Methane thiol | 91 | 21 | 77 | 52 | 43 |
| Ethane thiol | 85 | 32 | 62 | 58 | 32 |
| 2-Propane thiol | 50 | 30 | 40 | 41 | 18 |
| 2-Methyl-2-propane thiol | 7.3 | 5.4 | 26 | 6.7 | 8 |
| 1-Propane thiol | 21 | 10 | 52 | 17 | 19 |
| 2-Butane thiol | 45 | 32 | 29 | 41 | 9 |

EXAMPLE 5

The efficacy of N-(2-hydroxyethyl)-N,N-dimethyl-N-coco ammonium hydroxide in reducing 1-propane thiol in 50° C. kerosene fuel was compared to corresponding salts with various counter ions and with the corresponding internal salt (i.e., no counter ion). The 1-propyl mercaptan (1-propane thiol) content was measured 1 hour after treatment according to ASTM D-3227. The following results were obtained, wherein thiol content is the 1-propane thiol content given in ppm and % REDUCTION refers to the percentage reduction in 1-propane thiol content achieved. These results show better than a 20% improvement in scavenging with N-(2-hydroxyethyl)-N,N-dimethyl-N-coco ammonium hydroxide versus scavenging with N-(2-hydroxyethyl)-N,N-dimethyl-N-coco ammonium internal salt (35% reduction of 1-propane thiol versus 29% reduction of 1-propane thiol).

| COMPOSITION | THIOL CONTENT AFTER TREATMENT | % REDUCTION |
|---|---|---|
| Blank | 260.7 | |
| N-(2-hydroxyethyl)-N,N-dimethyl-N-coco ammonium hydroxide | 169.7 | 35 |
| N-(2-hydroxyethyl)-N,N-dimethyl-N-coco ammonium acetate | 229.6 | 12 |
| N-(2-hydroxyethyl)-N,N-dimethyl-N-coco ammonium chloride | 259.7 | 0 |
| N-(2-hydroxyethyl)-N,N-dimethyl-N-coco ammonium citrate | 230.6 | 12 |
| N-(2-hydroxyethyl)-N,N-dimethyl-N-coco ammonium bisulfate | 259.9 | 0 |
| N-(2-hydroxyethyl)-N,N-dimethyl-N-coco ammonium internal salt (no counter ion) | 184.3 | 29 |

EXAMPLE 6

The effect of the presence of air was investigated by adding 3000 ppm N-(2-hydroxyethyl)-N,N-dimethyl-N-coco ammonium hydroxide solution to two samples of 50° C. oilfield condensate, one of which was sparged with air prior to addition of the additive. The concentrations of various mercaptans in the feed and after treatment were measured after eight hours of storage and are given in the following table in ppm, as is the corresponding percentage reduction ("% RED'N").

| MERCAPTAN | CONTENT IN FEED | CONTENT AFTER TREATMENT (NO AIR) | % RED'N NO AIR | CONTENT AFTER TREATMENT (WITH AIR) | % RED'N WITH AIR |
|---|---|---|---|---|---|
| Methane thiol | 15 | 12 | 20 | 2 | 87 |
| Ethane thiol | 94 | 40 | 57 | 16 | 83 |
| 2-Propane thiol | 120 | 72 | 40 | 56 | 53 |
| 2-Methyl-2-propane thiol | 61 | 47 | 23 | 49 | 20 |
| 1-Propane thiol | 48 | 25 | 48 | 13 | 73 |
| 2-Butane thiol | 159 | 108 | 32 | 92 | 42 |
| 2-Methyl-1-propane thiol | 30 | 18 | 40 | 13 | 57 |
| 1-Butane thiol | 73 | 49 | 33 | 46 | 37 |
| 2-Methyl-3-butane thiol | 21 | 17 | 19 | 17 | 19 |
| 2-Pentane thiol | 58 | 39 | 33 | 37 | 36 |
| 3-Pentane thiol | 24 | 17 | 29 | 17 | 29 |

EXAMPLE 7

Solutions of N-(2-hydroxyethyl)-N,N-dimethyl-N-coco ammonium hydroxide were added to samples of crude oil in trials run at ambient temperatures, 50° C. and 75° C. The initial mercaptan concentration (0 min.) was measured, as was the mercaptan concentration five minutes, sixty minutes and 120 minutes after addition of the solution. The following table presents the results, giving the additive solution concentration and mercaptan concentrations ("RSH at __min.") in ppm.

|  | AMBIENT TEMPERATURE | | 50° C. | | 75° C. | |
|---|---|---|---|---|---|---|
| Additive Concentration | 1000 | 2000 | 1000 | 2000 | 1000 | 2000 |
| RSH at 0 min. | 743 | 743 | 727 | 727 | 757 | 757 |
| RSH at 5 min. | 701 | 640 | 661 | 645 | 714 | 549 |
| RSH at 60 min. | 581 | 521 | 573 | 541 | 533 | 505 |
| RSH at 120 min. | 518 | 517 | 458 | 434 | 420 | 354 |

EXAMPLE 8

Dimethylcocoamine was reacted with ethylene oxide in two reactions carried out under identical conditions, except that one reaction was carried out under anhydrous conditions, while the other was carried out in the presence of water. The resulting yield of quaternary compound (the internal salt for that prepared under anhydrous conditions and the hydroxide for that prepared in the presence of water) was measured at various times during the reaction and is presented in the following table in terms of milligrams of KOH per gram. The internal salt prepared under anhydrous conditions is identified as "ANH" and the hydroxide prepared in the presence of water is identified as "WATER".

| Yield at 30 minutes | | Yield at 60 minutes | | Yield at 90 minutes | |
|---|---|---|---|---|---|
| ANH | WATER | ANH | WATER | ANH | WATER |
| 57.3 | 65.0 | 59.4 | 67.6 | 63.1 | 68.2 |

EXAMPLE 9

Various quaternary compounds were prepared in the presence of water and under anhydrous conditions by ethoxylating tertiary amines. The concentrations of the resulting quaternary compound and the unreacted amine were measured upon completion of the reaction and the % yield was calculated. The results were as follows, with the concentration of the quaternary compound ("QUAT CONTENT") and the concentration of the unreacted amine ("UNREACTED AMINE CONTENT") being given in milli-equivalents per gram.

| AMINE | WATER? | QUAT. CONTENT | UNREACTED AMINE CONTENT | % YIELD |
|---|---|---|---|---|
| Dimethylcoco | Yes | 1.21 | 0.56 | 68 |
| Dimethylcoco | No | 1.27 | 0.62 | 67 |
| Dimethylbenzyl | Yes | 1.64 | 0.58 | 74 |
| Dimethylbenzyl | No | 1.73 | 0.97 | 64 |
| Methylmorpholine | Yes | 1.33 | 1.6 | 45 |
| Methylmorpholine | No | 1.45 | 1.87 | 44 |

Samples of the resulting compositions containing quaternary compounds were then added to 50° C. kerosene containing ethane thiol. The additive composition was added to the kerosene at a concentration of 500 ppm of the composition and the ethane thiol concentration at one hour after addition of the composition was measured according to ASTM D-3227. The following results were obtained, with the ethane thiol content being given in ppm.

| AMINE | WATER? | ETHANE THIOL CONTENT | % REDUCTION |
|---|---|---|---|
| Blank |  | 241 |  |
| Dimethylcoco | Yes | 173 | 28.22 |
| Dimethylcoco | No | 177 | 26.56 |
| Dimethylbenzyl | Yes | 201 | 16.60 |
| Dimethylbenzyl | No | 209 | 13.28 |
| Methylmorpholine | Yes | 219 | 9.13 |
| Methylmorpholine | No | 205 | 14.94 |

This procedure was repeated with different amounts of additive compositions, the amounts selected to adjust for the different level of quaternary compound in each composition. Sufficient composition was added in each run to achieve a 500 ppm concentration of actives in each test. The results were as follows.

| AMINE | WATER? | ACTUAL DOSE (ppm) | ETHANE THIOL CONTENT | % REDUCTION |
|---|---|---|---|---|
| Blank |  |  | 241 |  |
| Dimethylcoco | Yes | 715 | 153 | 36.51 |
| Dimethylcoco | No | 681 | 156 | 35.27 |
| Dimethylbenzyl | Yes | 527 | 199 | 17.43 |
| Dimethylbenzyl | No | 500 | 205 | 14.94 |
| Methylmorpholine | Yes | 650 | 214 | 11.20 |
| Methylmorpholine | No | 597 | 201 | 16.60 |

EXAMPLE 10

Further experiments were carried out with N-(2-hydroxyethyl)-N,N-dimethyl-N-coco ammonium hydroxide to test the effect of oxygen. The hydroxide was added at a concentration of 2000 ppm to each of two crude oil samples. Prior to the addition, one of the samples was sparged with air to produce an oxygen level of 75% of the stoichiometric level based on 750 ppm total mercaptans. The initial concentrations of various mercaptans in the samples were measured and their concentrations were measured again 1.5 hours after addition of the hydroxide. The following results were obtained, with the concentrations given in ppm.

| MERCAPTAN | INITIAL CONTENT | CONTENT 1 ½ HRS NO O₂ | % REDUCTION | CONTENT 1 ½ HRS WITH O₂ | % REDUCTION |
|---|---|---|---|---|---|
| Methane thiol | 97 | 69 | 28.87 | 15 | 84.54 |
| Ethane thiol | 75 | 56 | 25.33 | 22 | 70.67 |
| 2-Propane thiol | 41 | 36 | 12.20 | 22 | 46.34 |
| 1-Propane thiol | 17 | 14 | 17.65 | 6.7 | 60.59 |
| 2-Butane thiol | 37 | 35 | 5.41 | 24 | 35.14 |
| 2-Methyl-1-propane thiol | 3.8 | 3.9 | 0 | 2.1 | 44.74 |
| 2-Methyl-3-butane thiol | 3.5 | 3.2 | 8.57 | 2.6 | 25.71 |
| 2-Pentane thiol | 16 | 15 | 6.25 | 11 | 31.25 |
| 3-Pentane thiol | 7.7 | 7.4 | 3.90 | 5.9 | 23.38 |

Further tests were carried out on the influence of oxygen with addition of 2000 ppm N-(2-hydroxyethyl)-N,N-dimethyl-N-coco ammonium hydroxide in 50° C. crude oil containing 200 ppm 1-propane thiol. The test was conducted with four samples of the oil. No oxygen was added to one of the samples, oxygen at 50% of stoichiometry was added to a second sample, oxygen at 100% of stoichiometry was added to a third sample and oxygen at 200% of stoichiometry was added to the remaining sample. The percentage reduction in 1-propane thiol was determined for each sample seven hours after addition of the hydroxide with the following results.

| ADDED OXYGEN (% OF STOICHIOMETFY) | % 1-PROPANE THIOL REDUCTION |
|---|---|
| 0 | 16 |
| 50 | 28 |
| 100 | 51 |
| 200 | 57 |

EXAMPLE 11

Samples were prepared in hexane containing approximately 25 ppm MeSH, 25 ppm EtSH and 50 ppm PrSH. Each of two samples were treated with an equimolar amount (about 300 pm) of quaternary compound, one with the quaternary ammonium hydroxide (Petrolite product) and the other with the internal salt, the compounds having been prepared in Examples 1 and 2, above. An untreated blank was also prepared. The samples were heated at 60°–65° C. for one hour, analyzed by gas chromatography, allowed to stand at ambient temperature overnight, and analyzed again. The results are shown in the table below:

| SAMPLE | MeSH % DECREASE | EtSH % DECREASE | PrSH % DECREASE | TOTAL RSH DECREASE |
|---|---|---|---|---|
| Internal Salt, 1 hr., heat | 78.7 | 54.3 | 49.8 | 55.2 |
| Quat OH, 1 hr., heat | 71.4 | 51.5 | 48.1 | 52.4 |
| Internal Salt, 20 hr. | 76.5 | 51.1 | 44.5 | 50.5 |
| Quat OH, 20 hr. | 73.6 | 54.1 | 48.3 | 53.1 |

These results showed nominal differences within the margin of experimental error and so were inconclusive as to relative efficacy of the compositions.

It is believed that the lessening of some values overnight was due to inaccuracies in the method, as opposed to some sort of decomposition.

In view of the above, it will be seen that the several advantages of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A method for scavenging mercaptans in a hydrocarbon fluid, comprising adding to the fluid an effective mercaptan-scavenging amount of an aqueous scavenging composition comprising a quaternary ammonium hydroxide thereby to react the quaternary ammonium hydroxide with mercaptans in the fluid, the quaternary ammonium hydroxide being of the formula $R^1R^2R^3R^4NOH$, wherein $R^1$ and $R^2$ are independently selected from the group consisting of alkyl groups of from one to about eighteen carbon atoms, aryl groups of from six to about eighteen carbon atoms and alkylaryl groups of from seven to about eighteen carbon atoms, and $R^3$ is selected from the group consisting of alkyl groups of from two to about eighteen carbon atoms, aryl groups of from six to about eighteen carbon atoms and alkylaryl groups of from seven to about eighteen carbon atoms, provided, however, that $R^2$ and $R^3$ may be joined to form a heterocyclic ring including the N and optionally an oxygen atom, and $R^4$ is selected from the group consisting of —(CH₂CH₂O)ₙH, wherein n is an integer from one to about eighteen,

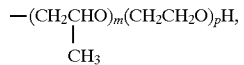

wherein m and p are independently selected from integers from zero to about eighteen, except that the sum m+p is at most about eighteen, and —CHR$^5$CHR$^6$Y, wherein R$^5$ and R$^6$ are independently selected from the group consisting of hydrogen, alkyl groups of from one to about eighteen carbon atoms, aryl groups of from six to about eighteen carbon atoms and alkylaryl groups of from seven to about eighteen carbon atoms, and Y is a non-acidic group selected from the group consisting of —OH, —SR$^7$ and —NR$^7$R$^8$, wherein R$^7$ and R$^8$ are independently selected from the group consisting of hydrogen, alkyl groups of from one to about eighteen carbon atoms, aryl groups of from six to about eighteen carbon atoms and alkylaryl groups of-from seven to about eighteen carbon atoms.

2. A method as set forth in claim 1 wherein R$^2$ and R$^3$ are not joined.

3. A method as set forth in claim 2 wherein R$^4$ is —CH$_2$CH$_2$OH.

4. A method as set forth in claim 1 wherein R$^1$ is methyl.

5. A method as set forth in claim 3 wherein R$^1$ and R$^2$ are each methyl.

6. A method as set forth in claim 5 wherein R$^3$ is coco.

7. A method as set forth in claim 1 wherein the hydrocarbon fluid contains some mercaptans of relatively low molecular weight and other mercaptans of relatively high molecular weight and the addition of the scavenging composition results in a greater proportional reduction of the mercaptans of relatively low molecular weight than of the mercaptans of relatively high molecular weight.

8. A method as set forth in claim 3 wherein the hydrocarbon fluid contains some mercaptans of relatively low molecular weight and other mercaptans of relatively high molecular weight and the addition of the scavenging composition results in a greater proportional reduction of the mercaptans of relatively low molecular weight than of the mercaptans of relatively high molecular weight.

9. A method as set forth in claim 1 wherein oxygen is also added to the hydrocarbon fluid.

10. A method as set forth in claim 1 wherein the hydrocarbon fluid is crude oil.

11. A method as set forth in claim 2 wherein the hydrocarbon fluid is crude oil.

12. A method as set forth in claim 3 wherein the hydrocarbon fluid is crude oil.

13. A method as set forth in claim 5 wherein the hydrocarbon fluid is crude oil.

14. A method as set forth in claim 1 wherein R$^4$ is selected from the group consisting of —(CH$_2$CH$_2$O)$_n$H, wherein n is an integer from one to about eighteen, and —CHR$^5$CHR$^6$Y, wherein R$^5$ and R$^6$ are independently selected from the group consisting of hydrogen, alkyl groups of from one to about eighteen carbon atoms, aryl groups of from six to about eighteen carbon atoms and alkylaryl groups of form seven to about eighteen carbon atoms, and Y is a non-acidic group selected from the group consisting of —OH, —SR$^7$ and —NR$^7$R$^8$, wherein R$^7$ and R$^8$ are independently selected from the group consisting of hydrogen, alkyl groups of from one to about eighteen carbon atoms and alkylaryl groups of from seven to about eighteen carbon atoms.

15. A method for scavenging mercaptans in a hydrocarbon fluid, comprising adding to the fluid an effective mercaptan-scavenging amount of an aqueous scavenging composition consisting essentially of water and a quaternary ammonium hydroxide of the formula R$^1$R$^2$R$^3$R$^4$NOH, wherein R$^1$ and R$^2$ are independently selected from the group consisting of alkyl groups of from one to about eighteen carbon atoms, aryl groups of from six to about eighteen carbon atoms and alkylaryl groups of from seven to about eighteen carbon atoms, and R$^3$ is selected from the group consisting of alkyl groups of from two to about eighteen carbon atoms, aryl groups of from six to about eighteen carbon atoms and alkylaryl groups of from seven to about eighteen carbon atoms, provided, however, that R$^2$ and R$^3$ may be joined to form a heterocyclic ring including the N and optionally an oxygen atom, and R$^4$ is selected from the group consisting of —(CH$_2$CH$_2$O)$_n$H, wherein n is an integer from one to about eighteen,

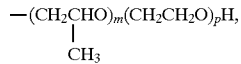

$$-(CH_2CHO)_m(CH_2CH_2O)_pH,$$
$$\phantom{-(CH_2C}|$$
$$\phantom{-(CH_2CHO)_m}CH_3$$

wherein m and p are independently selected from integers from zero to about eighteen, except that the sum m+p is at most about eighteen, and —CHR$^5$CHR$^6$Y, wherein R$^5$ and R$^6$ are independently selected from the group consisting of hydrogen, alkyl groups of from one to about eighteen carbon atoms, aryl groups of from six to about eighteen carbon atoms and alkylaryl groups of form seven to about eighteen carbon atoms, and Y is a non-acidic group selected from the group consisting of —OH, —SR$^7$ and —NR$^7$R$^8$, wherein R$^7$ and R$^8$ are independently selected from the group consisting of hydrogen, alkyl groups of from one to about eighteen carbon atoms and alkylaryl groups of from seven to about eighteen carbon atoms.

16. A method as set forth in claim 14 wherein R$^2$ and R$^3$ are not joined.

17. A method as set forth in claim 15 wherein R$^4$ is —CH$_2$CH$_2$OH.

18. A method as set forth in claim 14 wherein R$^1$ is methyl.

19. A method as set forth in claim 16 wherein R$^1$ and R$^2$ are each methyl.

20. A method as set forth in claim 18 wherein R$^3$ is coco.

21. A method as set forth in claim 14 wherein the hydrocarbon fluid contains some mercaptans of relatively low molecular weight and other mercaptans of relatively high molecular weight and the addition of the scavenging composition results in a greater proportional reduction of the mercaptans of relatively low molecular weight than of the mercaptans of relatively high molecular weight.

22. A method as set forth in claim 16 wherein the hydrocarbon fluid contains some mercaptans of relatively low molecular weight and other mercaptans of relatively high molecular weight and the addition of the scavenging composition results in a greater proportional reduction of the mercaptans of relatively low molecular weight than of the mercaptans of relatively high molecular weight.

23. A method as set forth in claim 14 wherein oxygen is also added to the hydrocarbon fluid.

24. A method as set forth in claim 14 wherein the hydrocarbon fluid is crude oil.

25. A method as set forth in claim 15 wherein the hydrocarbon fluid is crude oil.

26. A method as set forth in claim 16 wherein the hydrocarbon fluid is crude oil.

27. A method as set forth in claim 18 wherein the hydrocarbon fluid is crude oil.

28. A method as set in claim 15 wherein $R^4$ is selected from the group consisting of —$(CH_2CH_2O)_nH$, wherein n is an integer from one to about eighteen, and —$CH_2CH_2CHR^6Y$, wherein $R^5$ and $R^6$ are independently selected from the group consisting of hydrogen, alkyl groups of from one to about eighteen carbon atoms, aryl groups of from six to about eighteen carbon atoms and alkylaryl groups of form seven to about eighteen carbon atoms, and Y is a non-acidic group selected from the group consisting of —OH, —$SR^7$ and —$NR^7R^8$ wherein $R^7$ and $R^8$ are independently selected from the group consisting of hydrogen, alkyl groups of from one to about eighteen carbon atoms and alkylaryl groups of from seven to about eighteen carbon atoms.

* * * * *

UNITED STATES PATENT AND TRADEMARK OFFICE
CERTIFICATE OF CORRECTION

PATENT NO. : 5,840,177

DATED : November 24, 1998

INVENTOR(S) : Jerry Weers and David Gentry

Page 1 of 3

It is certified that error appears in the above-indentified patent and that said Letters Patent is hereby corrected as shown below:

col. 4, line 65-66; replace "non-aqueous" with ---aqueous---.

Claims:

In claim 1, at col. 15, line 14, delete the hyphen between "of" and "from";

In claim 16, at col. 16, line 36, replace "14" with ---15---;

In claim 17, at col. 16, line 38, replace "15" with ---16---;

In claim 18, at col. 16, line 40, replace "14" with ---15---;

In claim 20,m at col. 16, line 45, replace "18" with ---19---;

In claim 21, at col. 16, line 46, replace "14" with ---15---;

In claim 22, at col. 16, line 54, replace "16" with ---17---;

UNITED STATES PATENT AND TRADEMARK OFFICE
CERTIFICATE OF CORRECTION

PATENT NO. : 5,840,177
DATED : November 24, 1998
INVENTOR(S) : Jerry Weers and David Gentry It is certified that error appears in the above-indentified patent and that said Letters Patent is hereby corrected as shown below:

In claim 23, at col. 16, line 61, replace "14" with ---15---;

In claim 24, at col. 16, line 63, replace "14" with ---15---;

In claim 25, at col. 16, line 65, replace "15" with ---16---;

In claim 26, at col. 17, line 1, replace "16" with ---17---; and,

In claim 27, at col. 17, line 3, replace "18" with ---19---.

In claim 14, at col. 15, line 58, relace "form" with ---from---;

In claim 15, at col. 16, line 28, replace "form" with ---from---;

UNITED STATES PATENT AND TRADEMARK OFFICE
CERTIFICATE OF CORRECTION

PATENT NO. : 5,840,177
DATED : November 24, 1998
INVENTOR(S) : Jerry Weers and David Gentry It is certified that error appears in the above-indentified patent and that said Letters Patent is hereby corrected as shown below:

In claim 15, at col. 16, line 34, between the words "atoms" and "and", insert---, aryl groups of from six to about eighteen carbon atoms---; and, In claim 28, at col. 18, line 2, replace "form" with ---from---.

Signed and Sealed this

Twenty-third Day of November, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT NO. : 5,840,177
DATED : November 24, 1998
INVENTOR(S) : Weers, et. al.

It is certified that error appears in the above-identified patent and that said Letters Patent is hereby corrected as shown below:

At column 1, lines 6 and 7, the heading "1. Field of the Invention", should not be run-on after "BACKGROUND OF THE INVENTION", but should appear as a separate line on line 7;

At column 1, line 11, the heading "2. Description of Prior Art", should not be run-on after the sentence ending with the word"...scavengers", but should appear as a separate line on line 12; and At column 6, lines 34 and 35, the equations should appear as follows:

$$R^1R^2R^3R^4N^+OH^- + RSH \rightarrow RS^- + H_2O + R^1R^2R^3R^4N^+$$

$$2\,RS^- + O_2 \rightarrow RSSR\ (disulfide)$$

Signed and Sealed this

Fourteenth Day of December, 1999

Attest:

Q. TODD DICKINSON

Attesting Officer    Acting Commissioner of Patents and Trademarks